US007368104B2

(12) United States Patent
Bannister et al.

(10) Patent No.: US 7,368,104 B2
(45) Date of Patent: *May 6, 2008

(54) TREATMENT OF RESPIRATORY DISEASES

(75) Inventors: Robin Mark Bannister, Essex (GB); Andrew John McGlashan Richards, Cambridge (GB); Julian Clive Gilbert, Essex (GB); David A. V. Morton, Bath (GB); John Staniforth, Bath (GB)

(73) Assignee: Sosei R&D Ltd., Essex (GB)

( * ) Notice: Subject to any disclaimer, the term of this patent is extended or adjusted under 35 U.S.C. 154(b) by 193 days.

This patent is subject to a terminal disclaimer.

(21) Appl. No.: 10/926,196

(22) Filed: Aug. 24, 2004

(65) Prior Publication Data

US 2005/0019271 A1    Jan. 27, 2005

Related U.S. Application Data

(63) Continuation of application No. 10/266,717, filed on Oct. 7, 2002, which is a continuation-in-part of application No. PCT/GB01/01606, filed on Apr. 9, 2001.

(30) Foreign Application Priority Data

Apr. 7, 2000    (GB)    ................................ 0008660.3

(51) Int. Cl.
*A61K 9/12*    (2006.01)
*A61K 9/14*    (2006.01)
(52) U.S. Cl. .......................... 424/45; 424/46; 424/434; 424/489; 514/826; 514/851
(58) Field of Classification Search ................ 424/45, 424/46, 434, 489; 514/826, 851
See application file for complete search history.

(56) References Cited

U.S. PATENT DOCUMENTS

| | | | |
|---|---|---|---|
| 5,612,053 | A | 3/1997 | Baichwal et al. |
| 6,307,060 | B1 | 10/2001 | Noe et al. |
| 6,406,745 | B1 | 6/2002 | Talton |
| 6,613,795 | B2 | 9/2003 | Noe et al. |
| 6,645,466 | B1 | 11/2003 | Keller et al. |
| 2003/0068280 | A1* | 4/2003 | Bannister et al. ............ 424/46 |
| 2004/0028734 | A1* | 2/2004 | Bannister et al. .......... 424/468 |

FOREIGN PATENT DOCUMENTS

| WO | WO 97/39758 | 10/1997 |
|---|---|---|
| WO | WO 98/34595 | 8/1998 |
| WO | WO 00/06121 | 2/2000 |
| WO | WO 00/07567 | 2/2000 |
| WO | WO 00/28979 | 5/2000 |

OTHER PUBLICATIONS

Alex et al, American Journal of Critical Respiratory Care Medicine, 1999, 159(3); A823 (abstract/poster #A160).*
Boyars, M.C. "COPD in the ambulatory elderly: Management update." *Geriatrics.* Jun. 1988. 43(6): 29-32, 35-37, 40.
Cydulka, R.K. and C.L. Emerman. "Effects of combined treatment with glycopyrrolate and albuterol in acute exacerbation of chronic obstructive pulmonary disease." *Ann. Emerg. Med.* Apr. 1995 25(4): 470-473.
Disse, B., G.A. Speck, K.L. Rominger, T.J. Witek, Jr., and R. Hammer. "Tiotropium (Spiriva™): Mechanistical considerations and clinical profile in obstructive lung disease." *Life Sci.* 1999. 64(6-7): 457-464.
Haddad, B., H. Patel, J.E. Keeling, M.H. Yacoub, P.J. Barnes, and M.G. Belvisi. "Pharmacological characterization of the muscarinic receptor antagonist, glycopyrrolate, In human and guinea-pig airways." *Br. J. Pharmacol.* 1999. 127: 413-420.
Howder, C.L. "Antimuscarinic and βΓadrenoceptor bronchodilators in obstructive airways disease." *Respiratory Care.* Dec. 1993. 38(12): 1364-1388.
Leckie, M.J., S.A. Bryan, T.T. Hansel, and P.J. Barnes. "Novel therapy for COPD." *Exp. Opin. Invest Drugs.* 2000 9(1): 3-23.
Schroeckenstein, D.C., R.K. Bush, P. Chervinsky, W.W. Busse. "Twelve-hour bronchodilation in asthma with a single aerosol dose of the anticholinergic compound glycopyrrolate." *J. Allergy Clin. Immunol.* Jul. 1988. 82(1): 115-119.
Skorodin, M.S. "Pharmacotherapy for asthma and chronic obstructive pulmonary disease." *Arch Intern Med.* Apr. 12, 1993. 153: 814-828.
Tzelepis, G., S. Komanapoili, D. Tyler, D. Vega, and A. Fulambarker. "Comparison of nebulized glycopyrrolate and metaproterenol in chronic obstructive pulmonary disease." *Eur. Respir. J.* 1996. 9: 100-103.
Walker, IV, F.B., D.L. Kaiser, M.B. Kowal, and P.M. Suratt. "Prolonged effect of inhaled glycopyrrolate in asthma." *Chest.* Jan. 1987. 91(1): 49-51.
Ziment, I. "Pharmacologic therapy of obstructive airway disease." *Clin. Chest Med.* Sep. 1990. 11(3): 461-486.

* cited by examiner

*Primary Examiner*—Mina Haghighatian
(74) *Attorney, Agent, or Firm*—Saliwanchik, Lloyd & Saliwanchik

(57) ABSTRACT

A pharmaceutical composition for pulmonary delivery comprises glycopyrrolate in a controlled release formulation, wherein, on administration, the glycopyrrolate exerts its pharmacological effect over a period greater than 12 hours.

9 Claims, 2 Drawing Sheets

TREATMENT OF RESPIRATORY DISEASES

CROSS REFERENCE TO A RELATED APPLICATION

This application is a continuation application of co-pending application U.S. Ser. No. 10/266,717, filed Oct. 7, 2002; which is a continuation-in-part application of International Patent Application PCT/GB01/01606, filed Apr. 9, 2001; which claims priority to Great Britain Application No. 0008660.3, filed Apr. 7, 2000.

FIELD OF THE INVENTION

This invention relates to the treatment of respiratory diseases.

BACKGROUND OF THE INVENTION

Glycopyrrolate has been known for many years as an effective antimuscarinic agent. It has been used in several indications and been delivered by a number of different routes. It is currently used as an injectable primed to reduce secretions during anaesthesia and also as an oral product for treating gastric ulcers. One of the first descriptions of its use in airway disease was in 1984 where it was demonstrated to have a significant effect upon bronchodilation. Since then a number of studies have confirmed its potential utility.

Schroeckenstein et al., J. Allergy Clin. Immunol., 1988; 82(1): 115-119, discloses the use of glycopyrrolate in an aerosol formulation for treating asthma. A single administration of the metered-dose glycopyrrolate aerosol achieved bronchodilation over a 12 hour period.

Leckie et al., Exp. Opin. Invest. Drugs, 2000; 9(1): 3-23, is a general review of therapies for chronic obstructive pulmonary disease (COPD). Glycopyrrolate is mentioned as a possible drug treatment. However, there is no reference to its level of activity or to the duration at which it exerts its therapeutic effect.

Skorodin, Arch Intern. Med, 1993; 153: 814-828, discloses the use of glycopyrrolate in an aerosol formulation for the treatment of asthma and COPD. It is stated that, in general, the quaternary ammonium anticholinergic compounds have a duration of action of 4 to 12 hours. A dose of between 0.2 to 1.0 mg of glycopyrrolate is recommended at 6 to 12 hour intervals.

Walker et al., Chest, 1987; 91(1): 49-51, also discloses the effect of inhaled glycopyrrolate as an asthma treatment. Again, the duration of effective treatment is shown to be up to 12 hours, although up to 8 hours appears to be maximal.

WO-A-97/39758 discloses pharmaceutical compositions for treating respiratory inflammation containing the antioxidant tyloxapol. Page 23 refers to the addition of glycopyrrolate as an additional component in solution. There is no reference to the duration of activity of the glycopyrrolate, and the proposed effective dose (200-1000 μg) is similar to that described in the prior art above.

With this background, it is surprising to find that no glycopyrrolate formulation has been developed or registered for the treatment of airway disease. There are a number of possible reasons for this, and may include fears concerning systemic exposure and the drug binding at muscarinic receptors other than in the airways. This could result in both central and peripheral side-effects in patient populations that are already disposed to these complications. Such complications could be cardiovascular, ocular, mucosal or a predisposition to dizziness or fainting.

SUMMARY OF THE INVENTION

An object behind the present invention has been to develop an inhaled formulation which is a potent, effective, long-acting bronchodilator for the treatment of respiratory disease, in particular COPD. The pharmacodynamic and pharmacokinetic effects of the drug from the inhaled route will be controlled within a suitable formulation to ensure that the product is able to produce its effect following, preferably, once daily dosing.

According to a first aspect of the invention, a pharmaceutical composition for pulmonary delivery comprises an antimuscarinic agent such as glycopyrrolate that exerts a pharmacological effect over a period less than 12 hours, in a controlled release formulation, wherein, on administration, the formulation permits the agent to exert its pharmacological effect over a period greater than 12 hours.

As a composition of the invention is able to exert its therapeutic effect over a prolonged period, the patient will benefit from relief of symptoms for a longer period than with conventional antimuscarinic treatments. Furthermore, the patient may only require a once-a-day treatment regimen, and as this will usually avoid missed treatments, better compliance is expected. In addition, providing the agent in a controlled release formulation ensures that a lower initial peak of activity is achieved, which may result in reduced side effects associated with anticholinergic activity, for example dry mouth.

According to a further aspect of the invention, and which represents perhaps its most surprising finding, a dry powder formulation for pulmonary delivery comprises microparticles of glycopyrrolate. Such a formulation can itself be described as controlled release, providing a longer duration of action that has previously been found for this active agent.

According to another aspect of the invention, a particulate composition comprises discrete microparticles, each comprising an antimuscarinic agent held within a hydrophobic matrix material.

Formulating the antimuscarinic agent this way allows controlled release of the therapeutic so that the pharmacological effect is achieved over a period of time greater than 12 hours.

According to yet another aspect of the invention, the antimuscarinic is used in the manufacture of a medicament suitable for inhalation, for the treatment of a disease of the airways, the medicament being formulated so that one unit dose enables the agent to exert its pharmacological effect over a period greater than 12 hours.

According to a yet further aspect of the invention, a dry powder inhaler comprises a unit dose of an antimuscarinic agent in a controlled release formulation that permits the agent to exert its pharmacological effect over a period greater than 12 hours.

In each of the above aspects, the formulation is optimised for absorption and retention in the airways such that efficacy is maintained with systemic levels of drug at a concentration that does not cause significant side-effects in patients susceptible to muscarinic side-effects.

DESCRIPTION OF THE INVENTION

Figure 1:
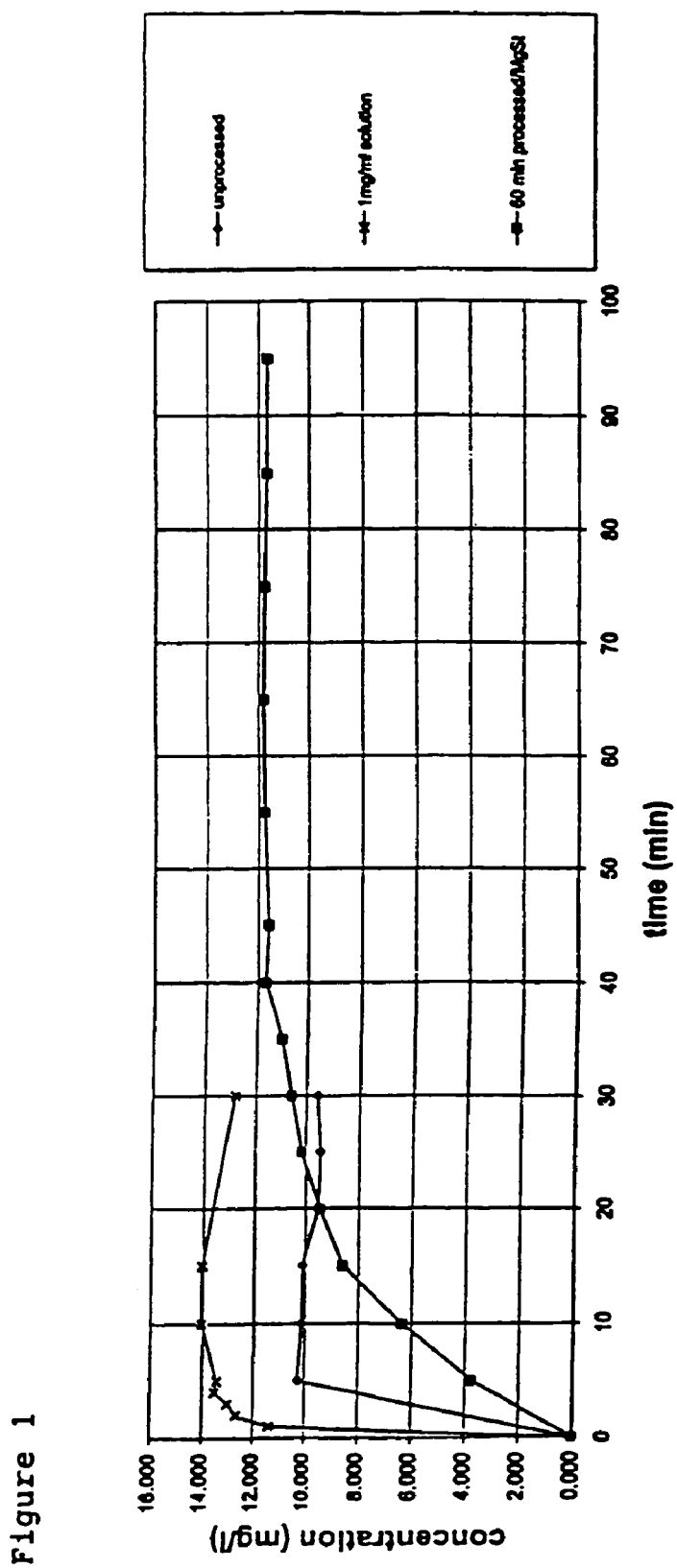
FIG. 1 illustrates the concentration of glycopyrrolate released over time, in a controlled release formulation.

The present invention relates to all antimuscarinic agents that normally exert their pharmacological effect over a period less than 12 hours. Glycopyrrolate is preferred, and the following description is in the context of glycopyrrolate formulations.

By means of the invention, glycopyrrolate can be used to treat airway disease, particularly COPD, asthma or cystic fibrosis. This may be effective in general. Further, particularly given that patients having such conditions often suffer from complications or are undergoing other therapies, this invention has utility in treating certain patient populations, e.g. those which may have sensitivity arising from cardiovascular, ocular or mucosal complications.

The reference to the "pharmacological effect" relates to the ability of the agent to relieve the symptoms of the airway disorder. This may be a measure of the $FEV_1$ levels, which are elevated in the presence of the agent when compared to that obtained in the absence of the treatment.

Conventional formulation technology may be used to achieve the controlled release composition. The important aspect is that the composition should have a duration of action greater than 12 hours, preferably more than 15 hours or 18 hours and most preferably more than 20 hours. This can be measured by techniques known to the skilled person, as shown below.

The controlled release formulations of glycopyrrolate are to be provided in a form suitable for delivery by inhalation. Devices and formulations suitable for delivery by inhalation are known to the skilled person. The composition may be prepared for delivery as an aerosol in a liquid propellant, for example for use in a pressurised metered dose inhaler (PMDI's). Propellants suitable for use in a PMDI are known to the skilled person, and include CFC-12, HFA-134a, HFA-227, HCFC-22 (difluorochloromethane), HFA-152 (difluoroethane and isobutane).

In a preferred embodiment of the invention, the compositions are in a dry powder form, for delivery using a dry powder inhaler (DPI). Dry powder inhalers are known. The dry powders for use in the inhalers will usually have a mass median aerodynamic diameter of less than 30 μm, preferably less than 20 μm and more preferably less than 10 μm. Microparticles having aerodynamic diameters in the range of 5 to 0.5 μm will generally be deposited in the respiratory bronchioles, whereas smaller particles having aerodynamic diameters in the range of 2 to 0.05 μm are likely to be deposited in the alveoli.

Having the glycopyrrolate in a controlled release formulation means that fewer doses are required, and subsequently inhalers may be provided with treatment packages that supply the glycopyrrolate over an extended number of treatment days compared to packages that have a similar number of doses per pack, but from which two or three doses are required each day.

In a preferred embodiment of the invention, the glycopyrrolate is formulated with a hydrophobic matrix material to form microparticles suitable for inhalation. The microparticles may be within the ranges specified above. Any pharmaceutically acceptable hydrophobic material may be used to formulate the microparticles, and suitable materials will be apparent to the skilled person. Preferred hydrophobic materials include solid state fatty acids such as oleic acid, lauric acid, palmitic acid, stearic acid, erucic acid, behenic acid, or derivatives (such as esters and salts) thereof. Specific examples of such materials include phosphatidylcholines, phosphatidylglycerols and other examples of natural and synthetic lung surfactants. Particularly preferred materials include metal stearates, in particular magnesium stearate, which has been approved for delivery via the lung.

The hydrophobic materials are resistant to immediate dissolution on administration, but are broken down over time to release the glycopyrrolate component.

The microparticles may also be formulated with additional excipients to aid delivery and release. For example, in the context of dry powder formulations, the microparticles may be formulated with additional large carrier particles which aid the flow from the dry powder inhaler into the lung. Large carrier particles are known, and include lactose particles having a mass median aerodynamic diameter of greater than 90 μm. Alternatively, the hydrophobic microparticles may be dispersed within a carrier material. For example, the hydrophobic microparticles may be dispersed within a polysaccharide matrix, with the overall composition formulated as microparticles for direct delivery to the lung. The polysaccharide acts as a further barrier to the immediate release of the glycopyrrolate component. This may further aid the controlled release process. Suitable carrier materials will be apparent to the skilled person and include any pharmaceutically acceptable insoluble or soluble material, including polysaccharides. An example of a suitable polysaccharide is xantham gum.

The compositions may also comprise additional therapeutic agents, either as separate components, i.e. as separate microparticles, or combined with the glycopyrrolate in the microparticles. In one embodiment, a therapeutic composition comprises the microparticles according to the invention, together with microparticles consisting of the glycopyrrolate, i.e. without any hydrophobic matrix material. This provides a composition that has a fast-acting component and a controlled-release component, and may provide effective relief quickly to a patient, together with a longer lasting effect. The fast-acting glycopyrrolate may be provided as additional microparticles, or may be dispersed, together with the hydrophobic microparticles, within a particle. For example, polysaccharide particles can be formulated with hydrophobic microparticles and fast-acting glycopyrrolate dispersed therein.

Controlled release formulations may be tested by methods known to those skilled in the art. Testing the formulations for release of glycopyrrolate in water may be used. Controlled release formulations will usually release 50% of the glycopyrrolate by dissolution in water over a period greater than 10 minutes, preferably greater than 20 minutes and most preferably greater than 30 minutes. During administration, the controlled release formulation may release the glycopyrrolate over a period greater than 12 hours, preferably 15 hours, more preferably 20 hours.

Any suitable pharmaceutically effective drug which is used for the treatment of a respiratory disease may also be co-administered with the glycopyrrolate compositions of the invention. For example, $\beta_2$-agonists, e.g. salbutamol, salmeterol and formetoral, may be formulated for co-administration with the glycopyrrolate compositions. Additional antimuscarinic compounds may also be co-administered. For example, ipratropium (e.g. ipratropium bromide) or tiotropium may be administered. Isomers, salt forms or counterion formulations of the antimuscarinic compounds are all within the scope of the present invention. These may be in their natural form or in a controlled release formulation. The natural form is preferred.

Additional therapeutics including steroids may also be co-administered. Examples of suitable steroids include beclomethasone, dipropionate and fluticasone. Other suitable therapeutics include mucolytics, matrix metalloproteinase inhibitors (MMPi's), leukotrienes, antibiotics, antineoplastics, peptides, vaccines, antitussives, nicotine, PDE4 inhibitors, elastase inhibitors and sodium cromoglycate.

Combination therapy may provide the maximal effect on FEV-1 and vital capacity. Co-administration of other drugs together with the slow release glycopyrrolate may also result in less side effects compared to co-administration with the conventional glycopyrrolate formulations, as there may be less contra-indications due to the late onset of activity of the glycopyrrolate.

Glycopyrrolate has two stereogenic centres and hence exists in four isomeric forms. Each individual isomer may be delivered to optimise the efficacious effect of the drug, and reduce systemic exposure to those isomers that are responsible for systemic side-effects.

A formulation of active isomers may be used, in which the ratio of isomers is 1:1, or less than 1:1. Alternatively, the formulation of active isomers is non-racemic, or the formulation ensures that the of active isomers are delivered at different rates.

Salt forms or counterion formulations of glycopyrrolate are within the scope of the present invention, e.g. glycopyrrolate bromide.

It is desirable that a formulation should be used, such that peak plasma levels related to systemic exposure are lower than previously, e.g. because of controlled release to give substantially constant plasma levels.

Compositions according to the invention may be produced using conventional formulation techniques. In particular, spray-drying may be used to produce the microparticles comprising the glycopyrrolate dispersed or suspended within a material that provides the controlled release properties.

The process of milling, for example, jet milling, may also be used to formulate the therapeutic composition. The manufacture of fine particles by milling can be achieved using conventional techniques. The term "milling" is used herein to refer to any mechanical process which applies sufficient force to the particles of active material to break or grind the particles down into fine particles. A wide range of milling devices and conditions are suitable for use in the production of the compositions of the inventions. The selection of appropriate milling conditions, for example, intensity of milling and duration, to provide the required degree of force will be within the ability of the skilled person. Ball milling is a preferred method. Alternatively, a high pressure homogeniser may be used in which a fluid containing the particles is forced through a valve at high pressure producing conditions of high sheer and turbulence. Sheer forces on the particles, impacts between the particles and machine surfaces or other particles, and cavitation due to acceleration of the fluid may all contribute to the fracture of the particles. Suitable homogenisers include the EmulsiFlex high pressure homogeniser, the Niro Soavi high pressure homogeniser and the Microfluidics Microfluidiser. The milling process can be used to provide the microparticles with mass median aerodynamic diameters as specified above. Milling the glycopyrrolate with a hydrophobic material is preferred, as stated above.

If it is required, the microparticles produced by the milling step can then be formulated with an additional excipient to produce particles with the hydrophobic microparticles dispersed therein. This may be achieved by a spray-drying process, e.g. co-spray-drying. In this embodiment, the hydrophobic microparticles are suspended in a solvent and co-spray-dried with a solution or suspension of the additional excipient. The spray-drying process will produce microparticles of a desired size which will comprise the hydrophobic microparticles dispersed therein. Preferred additional excipients include polysaccharides. Additional pharmaceutically effective excipients may also be used.

The amount of the active agent to be administered will be determined by the usual factors such as the nature and severity of the disease, the condition of the patient and the potency of the agent itself. These factors can readily be determined by the skilled man. The controlled release formulation is used to sustain the bronchodilatory effect over a prolonged period and raise the FEV levels. Following initial dosing, and subsequent doses, the $FEV_1$ level may be maintained at a level higher than that prior to the start of the therapy. It is desirable to provide sufficient active agent so that one unit dose will enable the glycopyrrolate to exert its pharmacological effect over a period greater than 12 hours, preferably greater than 15 or 18 hours, and more preferably greater than 20 hours. The amount of glycopyrrolate released over this period will be sufficient to provide effective relief (bronchodilation) of the respiratory disease, over this period. The measurement of bronchodilation may be carried out by techniques known to the skilled person, including spirometry. This may be used to measure the $FEV_1$ over the administration period. It is desirable to achieve a FEV, value that is greater than 10% of the predicted normal value, preferably greater than 20% and most preferably greater than 30%, over the administration period. The amount of glycopyrrolate in one unit dose may be similar to that disclosed in the prior art, e.g. 0.02-5 mg, preferably less than 2 mg, most preferably less than or about 1 mg. Larger or smaller doses may also be provided, for example, less than 100 μg. In the context of the microparticles, the glycopyrrolate may be present in, for example, greater than 20% by weight, preferably greater than 40% by weight, and more preferably greater than 60% by weight.

The following Examples illustrate the invention.

EXAMPLE 1

A mixture of micronised glycopyrrolate and magnesium stearate in the ratio 75:25 by mass (total mass of approximately 1 g) was placed in a ball mill on top of 100 g of 2 mm diameter stainless steel balls. The mill volume was approximately 58.8 ml. 5 ml of cyclohexane was added to wet the mixture. The mill was sealed and secured in a Retsch S100 centrifuge. Centrifugation was then carried out at 500 rpm for 240 minutes in total. Small samples (approximately 5-10 mg) of wet powder were removed from the mill every 60 minutes. The samples were dried in an oven at 37° C. under vacuum, prior to using the samples in a dissolution test.

The dissolution test was conducted with approximately 1 mg of micronised glycopyrrolate and approximately 1 mg of a ball milled glycopyrrolate/magnesium stearate mixture sampled after 60 minutes. A 195 ml reservoir was used in the dissolution test. The reservoir was filled with water and contained a sampling inlet port and a sampling outlet port. A sintered disk of approximately 50 mm diameter and 3 mm depth was placed in an opening on top of the reservoir, in contact with the water. A known mass (about 1 mg) of the sample to be tested was dropped onto the sinter and a timer started. At various times, 1 ml samples were removed from the reservoir and immediately replaced with 1 ml of water to maintain the volume in the system. The samples were analysed in a Cecil Aquarius CE7200 ultraviolet spectrophotometer at a wavelength of 200 nm. The concentration of the samples was calculated with a previously prepared calibration graph and the concentration versus time was plotted. To establish the base line diffusion characteristics of the system, a 1 ml solution containing 1 mg of glycopyrrolate was added to the system and the samples taken as above. The results are shown in FIG. 1.

FIG. 1 shows that the sample containing only glycopyrrolate exhibited a quick release of the glycopyrrolate into the reservoir, with the first time point at 5 minutes showing a concentration of greater than 10 mg/l. In contrast, the glycopyrrolate/magnesium stearate composition showed delayed release properties, with a concentration at 5 minutes of approximately 3.7 mg/l. The maximum concentration is achieved after 40 minutes in contrast to that of glycopyrrolate only, which achieves the maximum concentration at only 10 minutes.

EXAMPLE 2

A blend of micronised glycopyrrolate USP and lactose monohydrate (Pharmatose 150M, DMV, Veghel) as carrier was made by simple manual mixing, to give a concentration of 0.48% w/w glycopyrrolate. This was filled into hard gelatin capsules at two nominal fill weights, i.e.12.5 mg to give nominal 60 µg dose, and 25 mg to give a nominal 120 µg dose of glycopyrrolate. For the purpose of blinding, the capsules used were opacified with 2% w/w titanium dioxide (Capsugel Coni-Snap, Size 3, white opaque/white opaque, product code 1505).

For trials, doses were made up of one or more capsules. Thus, a 480 µg dose was given by using 4 of the 120 µg capsules.

A placebo was made by filling 25 mg of lactose into capsules. Placebo doses were given as the corresponding number of placebo capsules.

Six human patients exhibiting obstructive airways disease were administered 4×120 µg capsules in rapid succession via a Miat Monohaler. FEV1 was recorded, using standard spirometric techniques, in triplicate, frequently over 24 hours.

Figure 2:
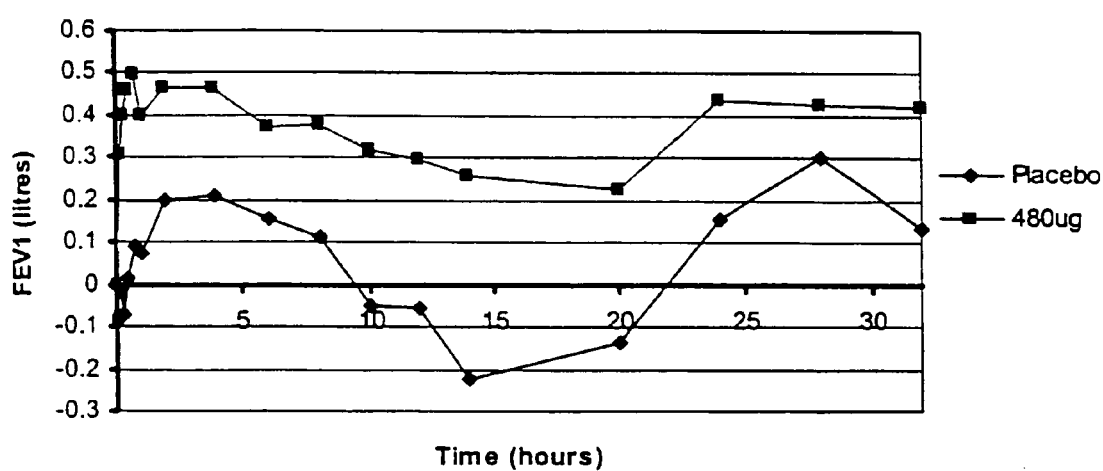
FIG. 2 shows the absolute change of FEV1 compared to baseline, for a dry powder formulation of the invention and also a placebo.

Results are shown in FIG. 2. Remarkably, the duration of action of the glycopyrrolate dry powder was significantly larger than for the placebo, over 24 hours. This is particularly surprising in view of the known characteristics of (nebulised) formulations of glycopyrrolate, showing a response within 2 to 12 hours.

We claim:

1. A method for treating a disease of the airways selected from a group consisting of asthma and cystic fibrosis, wherein said method comprises pulmonary delivery, to a patient in need of such treatment of a dry powder composition comprising microparticles of glycopyrrolate, wherein the composition is formulated so that one unit dose enables the glycopyrrolate to exert its pharmacological effect over a period of greater than 20 hours.

2. The method, according to claim 1, wherein the disease is asthma.

3. The method, according to claim 1, wherein the disease is cystic fibrosis.

4. The method according to claim 1, wherein the microparticles have a mass median aerodynamic diameter of less than 30 µm.

5. The method according to claim 1, wherein the composition additionally comprises large carrier particicles.

6. The method according to claim 5, wherein the large carrier particles are lactose particles having a mass median aerodynamic diameter of greater than 90 µm.

7. The method according to claim 1, wherein the composition further comprises a hydrophobic material.

8. The method, according to claim 7, wherein the hydrophobic material is magnesium stearate.

9. The method, according to claim 1, wherein a dose of less than 1 mg is administered to the patient.

* * * * *